US009458878B2

(12) United States Patent
Scatassa

(10) Patent No.: US 9,458,878 B2
(45) Date of Patent: Oct. 4, 2016

(54) BRACE FOR ARTICULATION

(71) Applicant: TECNOWAY SRL, Morciola di Colbordolo (IT)

(72) Inventor: Ettore Scatassa, Morciola di Colbordolo (IT)

(73) Assignee: TECNOWAY SRL, Morciola di Colbordolo (PU) (IT)

( * ) Notice: Subject to any disclaimer, the term of this patent is extended or adjusted under 35 U.S.C. 154(b) by 331 days.

(21) Appl. No.: 14/182,828

(22) Filed: Feb. 18, 2014

(65) Prior Publication Data

US 2014/0234016 A1 Aug. 21, 2014

(30) Foreign Application Priority Data

Feb. 21, 2013 (IT) ............................ RM2013A0100

(51) Int. Cl.
*F16C 11/10* (2006.01)
*A61F 5/01* (2006.01)

(52) U.S. Cl.
CPC ............. *F16C 11/10* (2013.01); *A61F 5/0102* (2013.01); *A61F 2005/0167* (2013.01); *Y10T 403/32426* (2015.01)

(58) Field of Classification Search
CPC ................. F16C 11/10; A61F 5/0102; A61F 2005/0167; Y10T 403/32; Y10T 403/32032; Y10T 403/32041; Y10T 403/32114; Y10T 403/32172; Y10T 403/32181; Y10T 403/32213; Y10T 403/32221; Y10T 403/32229
See application file for complete search history.

(56) References Cited

U.S. PATENT DOCUMENTS 2,812,961 A * 11/1957 Brown .................... A61F 2/582 403/93
4,463,751 A * 8/1984 Bledsoe ................ A61F 5/0123 602/16
4,540,306 A * 9/1985 Wang ........................ E06C 1/32 16/332
4,620,532 A * 11/1986 Houswerth ........... A61F 5/0125 602/16
4,770,559 A * 9/1988 Yoo ........................... E06C 1/32 182/163
4,817,588 A * 4/1989 Bledsoe ................ A61F 5/0125 602/16
4,846,842 A * 7/1989 Connolly .............. A61F 5/0125 602/16
4,982,732 A * 1/1991 Morris .................. A61F 5/0125 403/96
5,000,169 A * 3/1991 Swicegood ........... A61F 5/0125 128/882
5,052,379 A * 10/1991 Airy ...................... A61F 5/0125 482/112
5,062,858 A * 11/1991 Broeck ................. A61F 5/0123 602/16
5,292,303 A * 3/1994 Bastyr ................... A61F 5/0125 602/16

(Continued)

*Primary Examiner* — James Ference
(74) *Attorney, Agent, or Firm* — Steinfl & Bruno LLP

(57) ABSTRACT

A brace for articulation has a first rod, a second rod, and a joint connecting the two rods. The joint has a pair of circular toothed rings provided with a central hole and arranged overlapping. Each circular ring is fixed to one end of the first rod, which is interposed between them, the second rod being interposed between the circular rings. The joint also has a fixing central pivot, inserted in the central holes of the circular rings and into the through hole of said second rod. The joint further has a first and a second blocking member, each provided with a respective pin, adapted to be inserted in two overlapping throats of the indentation of the circular rings, to limit the movement of the second rod.

4 Claims, 3 Drawing Sheets

(56) References Cited

U.S. PATENT DOCUMENTS

| | | | | | |
|---|---|---|---|---|---|
| 5,399,154 | A * | 3/1995 | Kipnis | A61F 5/0125 | 602/16 |
| 5,409,449 | A * | 4/1995 | Nebolon | A61F 5/0125 | 16/333 |
| 5,419,754 | A * | 5/1995 | Hutchins | A61F 5/0123 | 602/16 |
| 5,421,810 | A * | 6/1995 | Davis | A61F 5/0123 | 602/16 |
| 5,437,611 | A * | 8/1995 | Stern | A61F 5/0125 | 482/124 |
| 5,443,444 | A * | 8/1995 | Pruyssers | A61F 5/0123 | 602/16 |
| 5,460,599 | A * | 10/1995 | Davis | A61F 5/0125 | 602/16 |
| 5,814,000 | A * | 9/1998 | Kilbey | A61F 5/0125 | 602/16 |
| 5,827,208 | A * | 10/1998 | Mason | A61F 5/0125 | 602/16 |
| 5,997,493 | A * | 12/1999 | Young | A61F 5/0125 | 602/16 |
| 6,080,122 | A * | 6/2000 | Gulledge | A61F 5/0125 | 602/16 |
| 6,527,733 | B1 * | 3/2003 | Ceriani | A61F 5/0123 | 602/16 |
| 6,623,439 | B2 * | 9/2003 | Nelson | A61F 5/0123 | 128/882 |
| 6,993,808 | B1 * | 2/2006 | Bennett | A61F 5/0125 | 16/321 |
| 7,037,287 | B2 * | 5/2006 | Cormier | A61F 5/0125 | 602/16 |
| 7,235,058 | B2 * | 6/2007 | Doty | A61F 5/0123 | 602/16 |
| 7,235,059 | B2 * | 6/2007 | Mason | A61F 5/0125 | 128/882 |
| 7,485,103 | B2 * | 2/2009 | Mason | A61F 5/0123 | 128/846 |
| 7,534,220 | B2 * | 5/2009 | Cormier | A61F 5/0125 | 135/141 |
| 7,841,999 | B2 * | 11/2010 | Napholz | A61F 5/0123 | 602/16 |
| 7,984,531 | B2 * | 7/2011 | Moore | A61F 5/0125 | 16/326 |
| 7,988,653 | B2 * | 8/2011 | Fout | A61F 5/013 | 24/593.1 |
| 8,172,781 | B2 * | 5/2012 | Oddou | A61F 5/0125 | 128/846 |
| 8,273,045 | B2 * | 9/2012 | Ceriani | A61F 5/0125 | 128/846 |
| 2002/0110406 | A1 * | 8/2002 | Coles | F16B 7/185 | 403/57 |
| 2004/0030275 | A1 * | 2/2004 | Morinaka | A61F 5/0125 | 602/27 |
| 2004/0267179 | A1 * | 12/2004 | Lerman | A61F 5/0125 | 602/26 |
| 2005/0215931 | A1 * | 9/2005 | Opahle | A61F 5/0125 | 602/23 |
| 2005/0240129 | A1 * | 10/2005 | Daiju | A61F 5/0125 | 602/16 |
| 2011/0314637 | A1 * | 12/2011 | Bejarano | A61F 5/0125 | 16/374 |

* cited by examiner

BRACE FOR ARTICULATION

CROSS REFERENCE TO RELATED APPLICATIONS

The present application claims priority to Italian Patent Application No. RM2013A000100 filed on Feb. 21, 2013 and incorporated herein by reference in its entirety.

FIELD

The present disclosure relates to a brace for articulation. More specifically, the disclosure concerns an ambidextrous brace, studied and realized in particular for post-traumatic or post-operative recovery of the elbow joint, but which can also be used for the knee joint, when supporting the knee after traumatic or post operating rehabilitation phases is necessary.

In the following, the description will be directed to an ambidextrous elbow joint brace, but it is clear that the same should not be considered limited to this specific use.

BACKGROUND

As it is well known, currently, in the case of elbow or distal humerus, or proximal of radius and ulna fractures, or elbow arthroscopy, wearing a brace to restrict and control the excursion degree of the elbow joint movements, also referred to by the acronym ROM ("Range of Motion"), is necessary for a patient.

In fact, during the recovery phase of the normal function of a joint of a patient, it is necessary that it is limited both in the flexion movement, i.e. the passage of the forearm from a position in which it forms a 90° angle with the arm to a position in which both form a 0° angle between them, as well as in the extension movement, in which there is the opposite passage, i.e. the passage of the forearm from a position which forms a 90° with the arm to a maximum extension position, in which it forms an angle of 180° with the arm.

Currently, there are braces comprising two rods coupled together by means of a rotary joint that can be blocked by means of buttons in order to maintain fixed rods between them at a predetermined angle.

The two rods are positioned with one on the arm and one on the forearm of the patient so that the rotary joint is in correspondence with the elbow and they are fixed to the patient's body through sheaths or sleeves with twist fasteners, snap or similar means.

A brace example according to the prior art is represented by U.S. Pat. No. 6,080,122, which relates to a brace for an arm comprising two rods connected to each other by a coupling comprising a circular ring, toothed along a circumference arc.

The ring is integral with one of the two arms while it is rotatably coupled with the second arm by means of a central pivot.

The ring is rotatably connected with a flat base through a central pivot. The flat base further includes a pivot that fits progressively along indentations of the ring circumference arc, corresponding to the rotation imparted on the flat base. Additional pivots block the excursion of the two rods so that when the flat base is rotated and fixed at a predetermined angle, the rods rotate accordingly by means of the toothed ring, and are blocked by locking pins. In this way, the patient's arm is fixed at a predetermined position, which inhibits the flexion and extension, thus limiting the ROM of the arm.

This brace, as well as other braces of the state of the art, allow arms to rotate between them according to a predetermined angle from 0° to 180° as they have indentations, guides or grooves that prevent a rotation of the rods between them at a higher angle.

It is evident then that limited mutual rotation of the rods results in a brace that can only be used for a right limb or a left limb but not both.

Moreover, the braces of the state of the art have joints composed of a plurality of mechanical elements such as pivots, rollers, elastic returning means and screws, which makes the structure of the joints complex.

It is evident, therefore, how easily a joint can be damaged due to failure even of a single pivot or a mechanical piece that composes such joint, thus requiring frequent maintenance of the brace.

SUMMARY

In light of the above, embodiments of the present disclosure provide an ambidextrous brace, which can then be used indifferently for both the articulation of a right or a left limb.

Several embodiments also provide a brace comprising a joint having a simple mechanical structure comprised of a few mechanical parts subject to wear and malfunction.

In particular, according to an aspect of the present disclosure, a brace for articulation is described, comprising a first rod, a second rod, having a through hole at one end, and a joint for connecting the first rod and the second rod, wherein the joint comprises a pair of circular toothed rings, provided with a central hole and arranged overlapping, each circular ring being fixed to one end of the first rod, the first and the second rod being interposed between the circular rings, a fixing central pivot, inserted in the central holes of the circular rings and into the through hole of the second rod, and a first and a second locking member each provided with a respective pin, adapted to be inserted in two overlapped throats of the indentation of the circular rings, so as to limit the movement of the second rod.

According to a further aspect of the disclosure, the brace can comprise adjustment means, capable of interacting with the first and second locking members, so as to rotate them, allowing the extraction and the insertion of respective pins from/into the overlapped throats of the indentation of the circular rings.

According to a further aspect of the disclosure, the first and second locking member can be rotatably mounted on one of the circular rings, each of the first and second locking member comprising an upper relief and two elastic facing arms, between which the fixing central pivot is placed, with the adjusting means comprising a first selector, capable to rotate around the fixing central pin, provided at the bottom with a seat, in which the upper relief of the first locking member is housed, and a second selector, provided at the bottom with a seat, in which the upper relief of the locking member is housed, the seats of the first and second selector and the upper reliefs of the first and second locking member being shaped in such a way that, by rotating the first or second selector, the respective pin is extracted from the overlapped throats of the indentation of the circular rings and, after the locking member has been rotated, the arms exert a return force as to allow the insertion of the respective pin in two overlapped throats of the indentation of the circular rings corresponding to the angle which the locking member has been rotated.

Advantageously, according to a further aspect of the disclosure, the upper reliefs of the locking member, can be "V"-shaped and the seats of each of the first or second selector can be "V"-shaped and have a size greater than the upper reliefs.

According to a further aspect of the disclosure, the first selector can provide a circle arc shaped opening on the surface, and a respective adjustment relief, while the second selector can be arranged above the first selector, such that the seat is slidably engaged with the opening, the second selector comprising a respective adjustment relief.

According to another aspect of the disclosure, the brace can comprise a knob, having one or more openings, to display the adjustment or the configurations of the joint, a circle arc shaped adjustment opening, and a plate, interposed between the knob and the second selector, in which adjustment graduated scales are shown, placed in correspondence of the one or more display openings of the knob, the adjustment reliefs being slidable along the adjustment opening.

BRIEF DESCRIPTION OF THE DRAWINGS

The present disclosure will be now described, for illustrative but not limitative purposes, according to its preferred embodiments, with particular reference to the figures of the enclosed drawings, wherein.

In the various figures, similar parts will be indicated by the same reference numbers.

DETAILED DESCRIPTION

Figure 1:
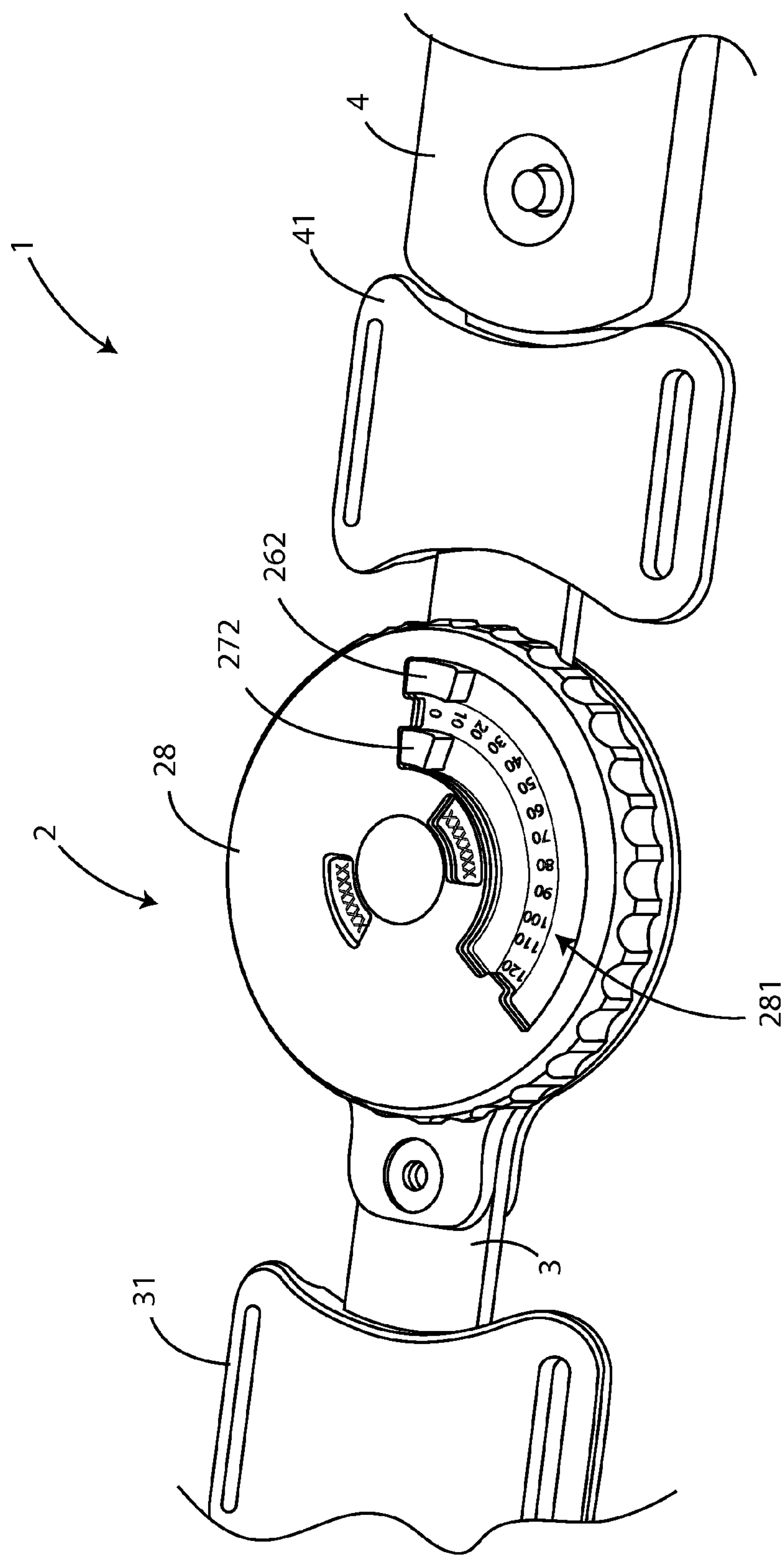
FIG. 1 shows a top perspective view of the brace for articulation according to the present disclosure.
Figure 2:
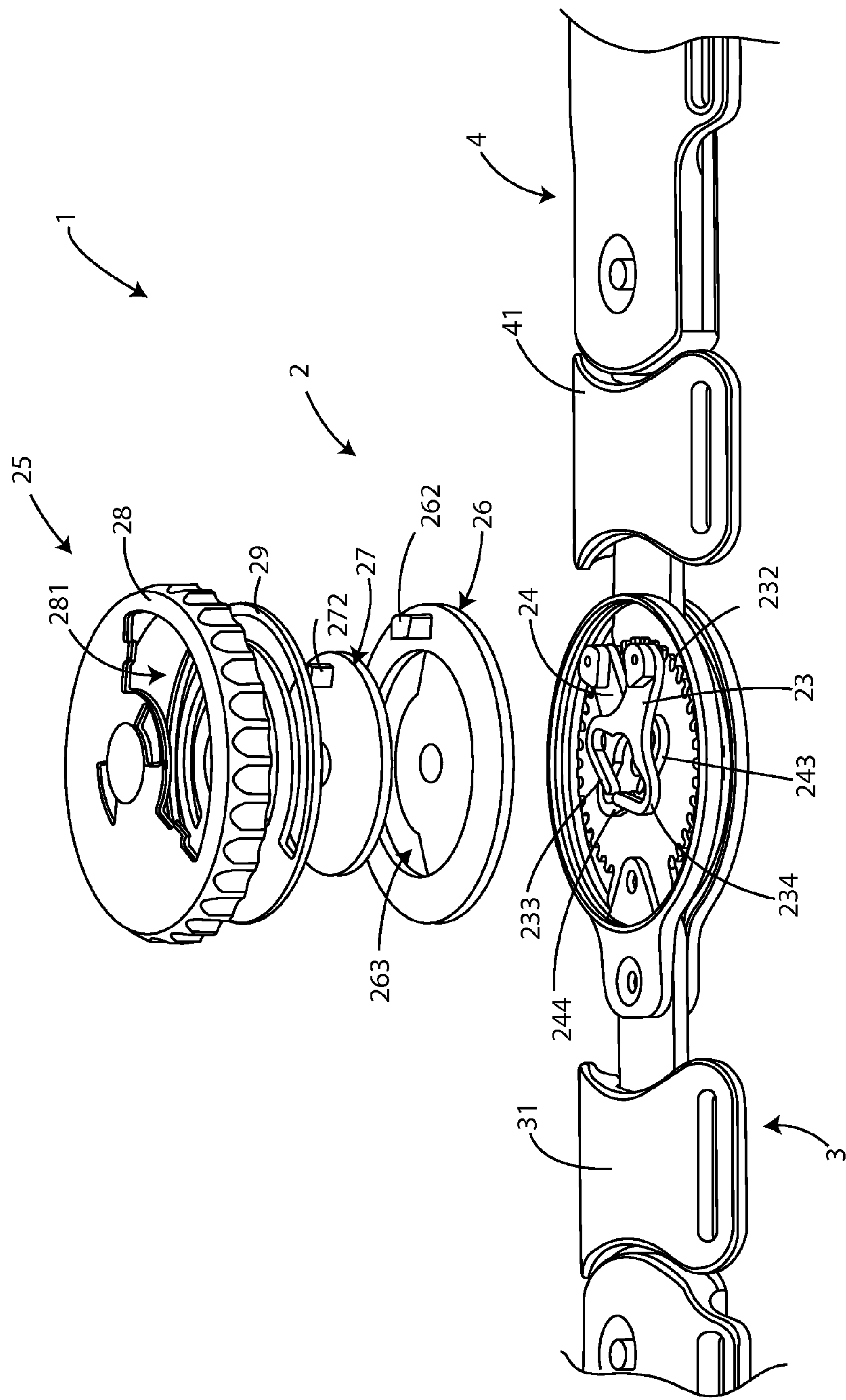
FIG. 2 shows an exploded view of the brace according to FIG. 1.
Figure 3:
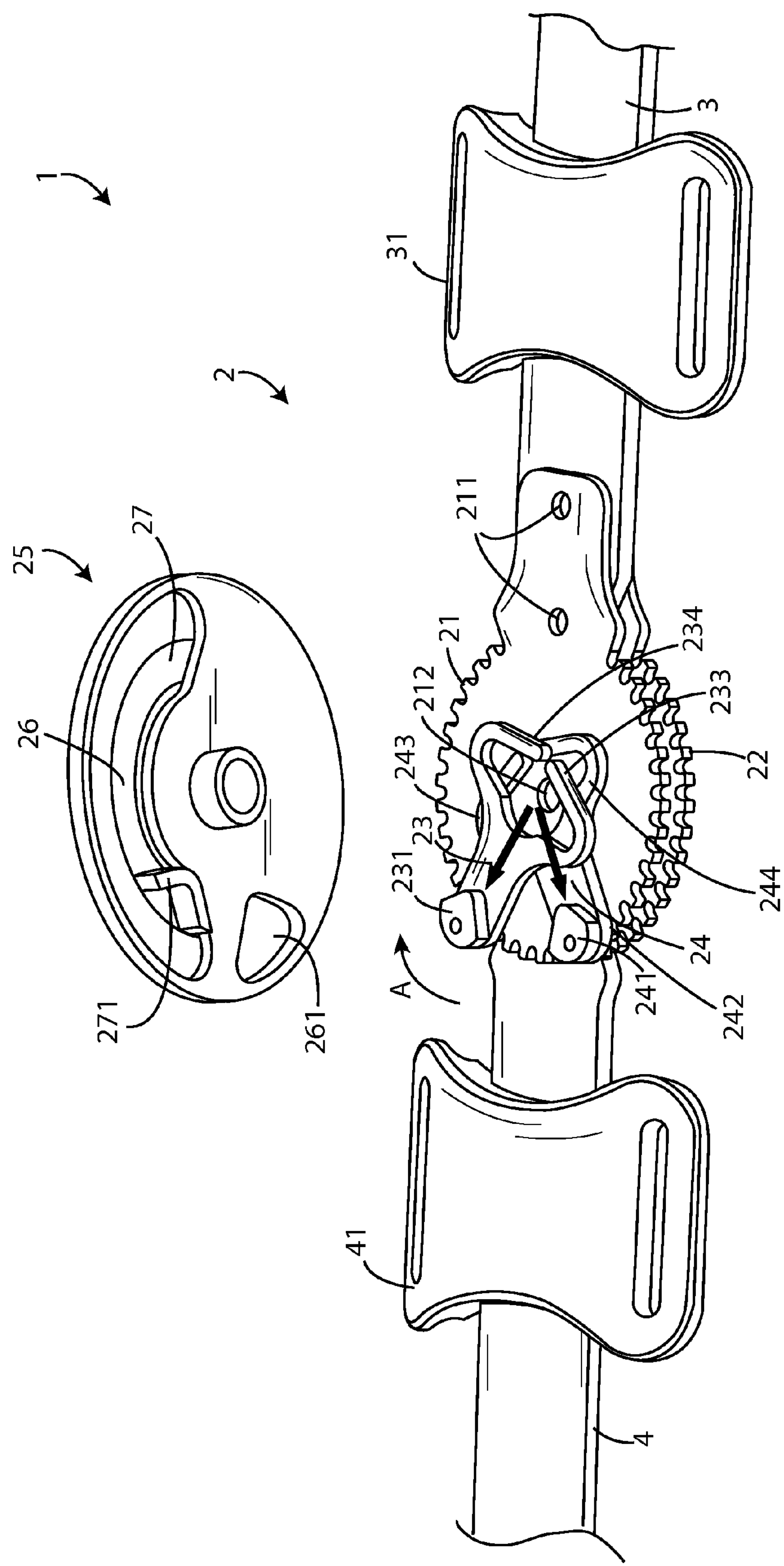
FIG. 3 shows a further detailed expanded view of the brace according to FIG. 1.

Referring to FIGS. 1-3, a brace for articulation 1 according to the present disclosure is observed.

The brace for articulation 1 includes a joint 2, a first rod 3 and a second rod 4. The joint 2 is interposed between the first rod 3 and the second rod 4 and allows their articulation.

The joint 2 comprises a pair of toothed circular rings 21 and 22, arranged overlapping, each fixed by means of suitable screws 211 to one end of the first rod 3, interposed between them. Each circular ring 21 and 22 has a central through hole, for allowing the insertion of a fixing central pivot (not shown in the figure). In the figures the through hole 212 of the circular ring 21 is shown.

The second rod 4 has a through hole at one end. The second rod 4 is inserted between the circular rings 21 and 22, and the fixing central pivot also passes through the through hole. In this way, the second rod 4 can rotate between the circular rings 21 and 22 with respect to the first rod 3.

On rods 3 and 4, buckles 31 and 41 are also arranged for securing the brace articulation 1 to the limb.

Joint 2 also comprises a first and a second locking member 23 and 24, each having a first and a second portion respectively.

The first portion of the first and second locking member 23 and 24 comprises an upper relief, respectively indicated with 231 and 241, which are "V"-shaped, and a respective pivot 232 and 242, adapted to be inserted into two overlapping throats of the indentation of the circular rings 21 and 22.

The lower portion of the first and second locking member 23 and 24 has two elastic facing arms, 233 and 234 (or 243 and 244), which identify an opening, through which the fixing central pivot of joint 2 passes, the function will be better explained in the following.

Joint 2 also includes adjustment means 25, interacting with the first and second locking member 23 and 24. The adjustment means 25 comprise a first selector 26, capable to rotate around the fixing central pivot, which is provided below with a seat 261, in which the upper relief 231 of the locking member 23 is housed, and, at the top, with an adjustment relief 262. The seat 261 is always "V"-shaped, as the upper relief 231 of the first locking member 23, with a greater size of it, for the reasons that will be better explained in the following. The first selector 26 also provides an opening 263 on the surface having the shape of a circle arc.

The adjustment means 25 also comprise a second selector 27, which is also capable of rotating around the fixing central pivot, below provided with a seat 271, in which the upper relief 241 of the second locking member 24 is housed. When the second selector 27 rotates with respect to the first selector 26, the seat 271 slides along the opening 263 of the first selector 26.

The seat 271, even in this case, is always "V"-shaped as the seat 261 of the locking member 23, and has a size greater than the respective upper relief 241, in which it is housed. The second selector 27 also includes an adjustment relief 272.

The adjustment means 25 comprise also a knob 28, having suitable openings, to display the adjustment or the configurations of the joint 2, and one plate 29, interposed between the knob 28 and the second selector 27, in which adjustment graduated scales are provided, placed in correspondence of the openings of the knob 28. The knob 28 has, in particular, one adjustment opening 281 having the form of a circle arc, in which the adjustment reliefs 262 and 272 can slide, which determines the rotation.

The operation of the brace for articulation 1 described above is as follows.

The figures show the initial configuration of the brace for articulation 1, in which the rods 3 and 4 are aligned and the first and the second locking member 23 and 24 have respective pivots 232 and 242 inserted in two throats of the two overlapping circular rings 21 and 22, such that the pivots of the first and second locking member 23 and 24 are in abutment with the rod 4, not allowing its movement, i.e. the rotation with respect to the first rod 3.

In this configuration, the first and the second selectors 26 and 27, and the knob 28, are arranged so as to indicate that the brace for articulation 1 is arranged for the left joint (elbow or knee, for example), and the adjustment reliefs 262 and 272 are arranged at the bottom of the scale, i.e. at one end of the adjustment opening 281, indicating 0° of flexion (rods 3 and 4 aligned) and 0° of extension (rod 4 fixed).

In this configuration, also, if the brace for articulation 1 were to be applied to the elbow, the first rod 3 would be aligned with the humerus, while the second rod 4 would be aligned with the ulna or with the radio.

The fact that the brace for articulation 1 is configured for a left limb, shows that knob 28 is arranged with respect to adjustment elements 262 and 272, so that locking members 23 and 24 can be rotated only in direction A, as adjustment reliefs 262 and 272 cannot slide in the opposite direction from the adjustment opening 281. Therefore, to move the locking member 24, the locking member 23 must be moved in direction A beforehand.

If allowing one flexion and/or extension of the movement of the joint is desired, then the first selector 26 is rotated to the desired angle in the arrow A direction, reading on the scale shown on plate 29, by acting on the adjustment relief 262. The seat 261 is shaped so as to move the upper relief 231 in the radial direction B, extracting the respective pivot 232 from the throats of the circular rings 21 and 22.

At the same time, arms 233 and 234, due to their elasticity, tend to exert a return force on the locking member 23, opposite to arrow B. After that the first locking member 23 is rotated to the desired position (i.e. the desired angle), due to the restoring force of arms 233 and 234, pivot 232 is inserted again into two new throats of the circular rings 21 and 22. In this way, rod 4 (and therefore the limb) can rotate by a rotation angle identified between the pivot 232 of the first locking member 23 and the pivot 242 of the second locking member 24.

Rotating the second locking member 24 in the direction A, acting on the adjustment relief 272 of the second selector 27, by the same mechanism described for the first locking member 23, it is possible to limit the flexion of the rod 4 and then of the limb. The second locking member 24 can be rotated at most by the same angle which the first locking member 23 is rotated. In particular, by rotating the second locking member 24 by the same angle of the first locking member 23, rod 4 is fixed with respect to the rod 3 of the angle.

In the case of the brace for articulation 1 were used for the other limb (right), starting from the initial configuration shown in the figures, knob 28 is rotated, so that the adjustment reliefs 262 and 272 are arranged in abutment to the other end of the adjustment opening 281, which determines the new end scale. Therefore, in this case, it will be possible to initially rotate the second locking member 24, for determining the flexion of rod 4 with respect to rod 3, i.e. of the limb, and only subsequently to rotate the first locking member 23, to reduce the flexion angle or to fix the angle between the rod 3 and the rod 4. Furthermore, by turning the knob 28, the openings are arranged so as to indicate the limb (right or left) for which joint 2 is configured.

Of course, even in this case the first rod 3 is aligned with the humerus and the second rod 4 with the ulna or with the radio.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A brace for articulation comprising:

a first rod, a second rod having a through hole at one end, a joint for connecting said first rod and said second rod, said joint comprising:

a pair of circular toothed rings, each comprising a central hole and arranged in an overlapping manner, each circular ring being fixed to one end of said first rod, said first rod and second rod being interposed between said circular rings, a fixing central pivot, inserted in said central holes of said circular rings and into said through hole of said second rod, and a first locking member provided with a first pin and a second locking member provided with a second pin, said first and second pins being configured for extraction from or insertion into two of a plurality of overlapping throats of an indentation of said circular rings, to limit movement of said second rod relative to the first rod, an adjustment means, configured to interact with said first and second locking members, so as to rotate said first or second locking members, allowing the extraction and the insertion of the first or the second pin respectively from or into the overlapping throats of the indentation of said circular rings, wherein:

said first and second locking members are rotatably mounted on one of said circular rings, each of said first and second locking members comprising an upper relief and two elastic facing arms, said fixing central pivot being placed between said two elastic facing arms, said adjustment means comprises a first selector, capable of rotating around said fixing central pin, provided at a bottom with a first seat, in which said upper relief of said first locking member is housed, and a second selector, provided at the bottom with a second seat, in which said upper relief of said second locking member is housed, and said seats of said first and second selectors and said upper reliefs of said first and second locking members are shaped in such a way that, by rotating said first or second selector, the first or second pin is respectively extracted from the overlapping throats of the indentation of said circular rings and, after the first and second locking member have been rotated, said arms exert a return force as to allow respective insertion of the first or second pin in two of the plurality of overlapping throats of the indentation of said circular rings corresponding to an angle by which said locking member has had been rotated.

2. The brace according to claim 1, wherein said upper reliefs of said locking members are Y-shaped and said seats of each of said first or second selector are Y-shaped and have a size greater than said upper reliefs.

3. The brace according to claim 1, wherein:

said first selector comprises an opening circular arc on a surface of the first selector, and a respective one of said adjustment reliefs, and said second selector is arranged above said first selector, such that said second seat is slidably engaged with said opening, said second selector comprising a respective one of said adjustment reliefs.

4. The brace according to claim 3, further comprising:

a knob, having one or more openings, to display adjustment or configurations of said joint, a circle arc shaped adjustment opening, and a plate, interposed between said knob and said second selector, in which adjustment graduated scales are shown, placed in correspondence of said one or more display openings of said knob, wherein said adjustment reliefs are slidable along said adjustment opening.

* * * * *